(12) United States Patent
Krijnsen et al.

(10) Patent No.: US 8,062,287 B2
(45) Date of Patent: Nov. 22, 2011

(54) DEVICE FOR CONTROLLED RELEASE OF CHEMICAL MOLECULES

(75) Inventors: Hendrika Cecilia Krijnsen, Boxtel (NL); Geert Langereis, Eindhoven (NL); Michel Paul Barbara Van Bruggen, Helmond (NL); Ventzeslav Petrov Iordanov, Valkenswaard (NL)

(73) Assignee: Koninklijke Philips Electronics N V, Eindhoven (NL)

( * ) Notice: Subject to any disclaimer, the term of this patent is extended or adjusted under 35 U.S.C. 154(b) by 18 days.

(21) Appl. No.: 12/158,059

(22) PCT Filed: Dec. 12, 2006

(86) PCT No.: PCT/IB2006/054769
§ 371 (c)(1),
(2), (4) Date: Jun. 19, 2008

(87) PCT Pub. No.: WO2007/072297
PCT Pub. Date: Jun. 28, 2007

(65) Prior Publication Data
US 2008/0262478 A1    Oct. 23, 2008

(30) Foreign Application Priority Data

Dec. 22, 2005 (EP) .................... 05112686

(51) Int. Cl.
*A61K 9/22* (2006.01)
(52) U.S. Cl. .............. 604/890.1; 604/891.1; 604/31; 604/65; 604/66; 604/67; 604/503

(58) Field of Classification Search ............ 604/31, 604/65–67, 503, 890.1, 891.1
See application file for complete search history.

(56) References Cited

U.S. PATENT DOCUMENTS

| 4,392,849 | A  | * | 7/1983  | Petre et al. ................ 604/66 |
| 4,403,984 | A  |   | 9/1983  | Ash et al. |
| 5,582,168 | A  |   | 12/1996 | Samuels et al. |
| 6,016,444 | A  | * | 1/2000  | John ...................... 600/544 |
| 6,424,847 | B1 | * | 7/2002  | Mastrototaro et al. ...... 600/316 |
| 6,632,216 | B2 |   | 10/2003 | Houzego et al. |
| 2002/0198470 | A1 | * | 12/2002 | Imran et al. ............. 600/587 |
| 2004/0158194 | A1 |   | 8/2004  | Wolff et al. |
| 2004/0220460 | A1 | * | 11/2004 | Roberts ................. 600/333 |
| 2004/0253304 | A1 | * | 12/2004 | Gross et al. ............. 424/451 |
| 2005/0058701 | A1 |   | 3/2005  | Gross et al. |
| 2007/0208263 | A1 | * | 9/2007  | John et al. .............. 600/509 |

FOREIGN PATENT DOCUMENTS

| JP | 04041420 A    | 2/1992 |
| JP | 2002186672    | 7/2002 |
| WO | 2004026281 A2 | 4/2004 |
| WO | 2004066903 A2 | 8/2004 |
| WO | 2006056944 A1 | 6/2006 |
| WO | 2006077528 A2 | 7/2006 |

OTHER PUBLICATIONS

Viswanathan, S.: "Timing Is Everything"; Downloaded From WWW. PHARMAQUALITY.COM/FEATURE7a.HTM on Jul. 24, 2005, 2 page Document.

* cited by examiner

*Primary Examiner* — Bhisma Mehta
*Assistant Examiner* — Larry R Wilson

(57) ABSTRACT

The invention relates to a device comprising an ingestible capsule which measures at least one body parameter and starts a drug release program upon predefined changes in the body parameter.

19 Claims, 2 Drawing Sheets

DEVICE FOR CONTROLLED RELEASE OF CHEMICAL MOLECULES

This invention is in the field of devices for drug administration.

Most biological functions and processes are anything but constant. Instead, often a prominent, genetically based time structure consisting of rhythms is observed.

The concept of homeostasis stipulates that there is constancy of the endogenous compounds in blood. This is a most powerful construct in biology, and has influenced not only the teaching and understanding of medical science but also the practice of clinical medicine. According to this concept, the risk of occurrence and exacerbation of disease is independent of the time of day, day of the month, and month of the year, as is the response of patients to diagnostic tests and medications. However, findings from the field of biological rhythm studies (chronobiology) challenge the concept of homeostasis as well as many of the assumptions and procedures of clinical medicine.

Many biological functions wax and wane in cycles that repeat on a daily, monthly, or annual basis. Such patterns do not reflect simply an organism's passive response to environmental changes, such as daily cycles of light and darkness. Rather, they reflect the organism's biological rhythms, that is, its ability to keep track of time and to direct changes in function accordingly.

It is therefore an object of the present invention to provide a device for drug administration which is for most applications capable of responding to the periodic changes in biological functions over time.

According to this, a device for drug administration is provided, comprising:
a) a measuring means which measures at least one body parameter of the patient for at least ≧1 measuring cycles and at least ≧1 monitoring cycle,
b) a normalizing means which generates a normalized curve for each of the measured body parameter(s) of the patient from the data obtained in the measuring cycles and adjusts the data obtained in the at least one monitoring cycle to normalized data based on the normalized curve so as to obtain normalized monitoring data, and
c) an ingestible capsule which comprises a drug release means which starts a drug release program when during the at least ≧1 monitoring cycle a change of ≧25%/hour (on the normalized scale) has been observed in the normalized monitoring data for a period of ≧1 hour and/or the normalized monitoring data deviates from a preselected point on the normalized curve by a threshold value of ≦50% (on the normalized scale).

At least one of the following advantages is achieved thereby for most of the applications within the scope of the present invention:
the drug release means starts a drug release program upon an observation of a change in the body parameter as described above, so the drug can be released in an improved time frame for most applications, thus reducing side effects and improving the effectiveness of the drug for most applications,
the daily amount of drug to be administered outside the effective window may be lowered, thus limiting side effects of the drug,
the release of the drug can be personalized/individualized in dependence on the patient's needs based on the patient's own rhythm, and
discrete (or pulsed, or periodic) administering is found to have a lower body anticipation rate than continuous administering.

The term "measuring cycle" means and/or includes especially that a patient's body parameter is measured which is known to behave in a cyclic and/or periodic manner, e.g. the body temperature. A measuring cycle in the sense of the present invention may last a day (circadian), but longer (e.g. infradian) and/or shorter cycles (ultradian) are also feasible and also form part of embodiments of the present invention. According to an embodiment of the present invention, no drug is dispensed by the device during the measuring cycle.

The term "normalizing curve" means and/or includes especially that the normalizing curve is calculated from the data derived from the measuring cycles by the equation:

$$Z = (X - \text{mean}(X))/\text{standard deviation} \ast 100\%$$

with X (also written as $X_t$) being the body parameter and mean(X) being the mathematical average of $X_t$ over a defined period. It should be noted that usually X can have positive as well as negative values.

The data used in this application is presented in % on a normalized scale; but it goes without saying that this is merely for the sake of better understanding and any person skilled in the art may easily transform the data to any given scale known in the field.

The term "monitoring cycle" means and/or includes especially that during this cycle the drug release means is started, e.g. that during this cycle a drug may be released (possibly after a certain delay). A monitoring cycle in the sense of the present invention may last a day (circadian), but longer (e.g. infradian) and/or shorter cycles (ultradian) are also feasible and form part of embodiments of the present invention.

It goes without saying that the data obtained in this monitoring cycle may be used for normalization of the curve as well, so some of the monitoring cycles are measuring cycles and vice versa in an embodiment of the present invention.

The term "drug release program" means and/or includes that a certain, predefined amount of a drugs or a mixture of drugs is released when the change in the body parameter as described above is observed. It should be mentioned that this drug release need not be instantaneous, rather according to an embodiment of the present invention, the drug is released after a predefined delay (as will be described in more detail later on).

According to an embodiment of the present invention, in a case in which several body parameters are measured by the measuring means, the drug release program may be started when all body parameters show a change as described above. However, according to an embodiment of the present invention, the drug release program is started when only one (or more) of the body parameters, but not necessary all, show the change as described above.

It should be noted that, according to an embodiment of the present invention, the measuring and normalizing means are included in the ingestible capsule, whereas according to another embodiment of the present invention, they are separate from the capsule. In the latter case, according to an embodiment of the present invention, the data and/or a start signal are transferred to the capsule in order to start the drug release program when needed.

According to an embodiment of the present invention, the drug release means starts a drug release program when during the at least ≧1 monitoring cycle a change of ≧50%/hour (on the normalized scale) has been observed in the normalized monitoring data for a period of ≧1 hour.

It should be noted that a "change" (of one or more monitored parameters) according to the present invention includes a rise and or a decline in the normalized curve. Depending on the actual indication, the drug release program may start when a rise is detected only, or only in case of a decline, or on both occasions.

According to an embodiment of the present invention, the drug release program may start when a rise is detected only (in the behavior of one or several parameter(s)), or only in case of a decline (in the behavior of one or several parameter(s)), or on both occasions (in the behavior of one or several parameter(s)), or on any combination (with parameters $\geq 1$).

According to an embodiment of the present invention, the drug release means starts a drug release program when during the at least $\geq 1$ monitoring cycle a change of $\geq 40\%$/hour (on the normalized scale) has been observed in the normalized monitoring data for a period of $\geq 3$ hours.

According to an embodiment of the present invention, the drug release means starts a drug release program when during the at least $\geq 1$ monitoring cycle a change of $\geq 30\%$/hour (on the normalized scale) is observed in the normalized monitoring data for a period of $\geq 4$ hours.

According to an embodiment of the present invention, the drug release means starts a drug release program when during the at least $\geq 1$ monitoring cycle a change of $\geq 25\%$/hour (on the normalized scale) has been observed in the normalized monitoring data for a period of $\geq 5$ hours.

According to an embodiment of the present invention, the drug release means starts a drug release program when during the at least $\geq 1$ monitoring cycle a change of $\geq 20\%$/hour (on the normalized scale) has been observed in the normalized monitoring data for a period of $\geq 6$ hours.

According to an embodiment of the present invention, the drug release means starts a drug release program when during the at least $\geq 1$ monitoring cycle the normalized monitoring data deviates from the normalized 0%-point of the normalized curve by a threshold value of $\leq 50\%$ (on the normalized scale).

According to an embodiment of the present invention, the drug release means starts a drug release program when during the at least $\geq 1$ monitoring cycle the normalized monitoring data deviates from the normalized 0%-point of the normalized curve by a threshold value of $\leq 25\%$.(on the normalized scale).

According to an embodiment of the present invention, the drug release means starts a drug release program when during the at least $\geq 1$ monitoring cycle the normalized monitoring data deviates from the normalized 0%-point of the normalized curve by a threshold value of $\leq 10\%$ (on the normalized scale).

According to an embodiment of the present invention, the drug release means starts a drug release program when during the at least $\geq 1$ monitoring cycle the normalized monitoring data deviates from the minimum point of the normalized curve by a threshold value of $\leq 50\%$ (on the normalized scale).

According to an embodiment of the present invention, the drug release means starts a drug release program when during the at least $\geq 1$ monitoring cycle the normalized monitoring data deviates from the minimum point of the normalized curve by a threshold value of $\leq 25\%$ (on the normalized scale).

According to an embodiment of the present invention, the drug release means starts a drug release program when during the at least $\geq 1$ monitoring cycle the normalized monitoring data deviates from the minimum point of the normalized curve by a threshold value of $\leq 10\%$ (on the normalized scale).

According to an embodiment of the present invention, the drug release means starts a drug release program when during the at least $\geq 1$ monitoring cycle the normalized monitoring data deviates from the maximum point of the normalized curve by a threshold value of $\leq 50\%$ (on the normalized scale).

According to an embodiment of the present invention, the drug release means starts a drug release program when during the at least $\geq 1$ monitoring cycle the normalized monitoring data deviates from the maximum point of the normalized curve by a threshold value of $\leq 25\%$ (on the normalized scale).

According to an embodiment of the present invention, the drug release means starts a drug release program when during the at least $\geq 1$ monitoring cycle the normalized monitoring data deviates from the maximum point of the normalized curve by a threshold value of $\leq 10\%$ (on the normalized scale).

According to an embodiment of the present invention, the at least one body parameter includes body temperature, core body temperature, skin surface temperature, blood pressure, melatonin level, triacylglycerol level, cortisol level.

According to an embodiment of the present invention, the drug release program includes a delay of $\geq 0$ and $\leq 24$ hours prior to the release of drugs.

According to an embodiment of the present invention, the drug release program includes a delay of $\geq 0$ and $\leq 2$ measuring and/or monitoring cycles, according to an embodiment $\geq 0$ and $\leq 1$ measuring and/or monitoring cycles, prior to the release of drugs.

According to an embodiment of the present invention, the drug release program is stopped after $\geq 1$ and $\leq 30$ cycles. According to an embodiment of the present invention, the drug release program is stopped after $\geq 5$ and $\leq 20$ cycles.

Alternatively, however, according to an embodiment of the present invention, the monitoring and/or measuring is done continuously, i.e. the number of monitoring and/or measuring cycles is not limited.

According to a different embodiment of the present invention, the drug release is stopped when during the at least $\geq 1$ monitoring cycle a change of $\geq 30\%$/hour (on the normalized scale) has been observed in the normalized monitoring data for a period of $\geq 4$ hours.

According to an embodiment of the present invention, the drug release is stopped when during the at least $\geq 1$ monitoring cycle the normalized monitoring data deviates from the minimum point of the normalized curve by a threshold value of $\leq 25\%$.

According to an embodiment of the present invention, the drug release program is stopped when the normalized monitoring data return to between $\geq -60\%$ and $\leq 60\%$.

The present invention also relates to a method for the controlled release of drugs, comprising the steps of a) measuring at least one body parameter of the patient for at least $\geq 1$ measuring cycles and at least $\geq 1$ monitoring cycle, b) generating a normalized curve for each of the measured body parameter(s) of the patient from the data obtained in the measuring cycles and adjusting the data obtained in the at least one monitoring cycle to normalized data based on the normalized curve so as to obtain normalized monitoring data, and c) starting a drug release program when during the at least $\geq 1$ monitoring cycle a change of $\geq 25\%$ has been observed in the normalized monitoring data for a period of one hour and/or the normalized monitoring data deviates from a preselected point of the normalized curve by a threshold value of ≦50%.

According to an embodiment of the present invention, the drug release program includes a delay of ≧0 and ≦24 hours prior to the release of drugs.

According to an embodiment of the present invention, the drug release program includes a delay of ≧0 and ≦2 measuring cycles, according to an embodiment ≧0 and ≦2 measuring cycles, prior to the release of drugs.

A device according to the present invention may be of use in a wide variety of systems and/or applications, amongst them one or more of the following:
  medical devices for the administering of drugs,
  medical devices for the treatment of chronic diseases.

The aforementioned components, as well as the claimed components and the components to be used in accordance with the invention in the described embodiments, are not subject to any special exceptions with respect to their size, shape, material selection, and technical concept such that the selection criteria known in the pertinent field can be applied without limitations.

BRIEF DESCRIPTION OF THE DRAWINGS

Additional details, features, characteristics and advantages of the subject of the invention are disclosed in the dependent claims, the Figures and the following description of these Figures, Tables and examples, showing several embodiments of a device as well as a device according to the invention by way of example.

FIG. 1 is a highly schematic cross-sectional view of a device 1 according to a first embodiment of the present invention. This device in the form of an ingestible capsule comprises a measuring means 10 which is capable of measuring several body parameters. The relevant data are stored and normalized in a central control unit 30, which stores them and generates a normalized curve from the measured data. The measuring means 10 continues to measure data steadily and deliver them to the central control unit 30. Upon a change in the measured data as described above, the central control unit starts a drug release program. For this purpose, it is assisted by a timer 40, which causes the delivery of drugs to start after a certain delay.

Figure 1:
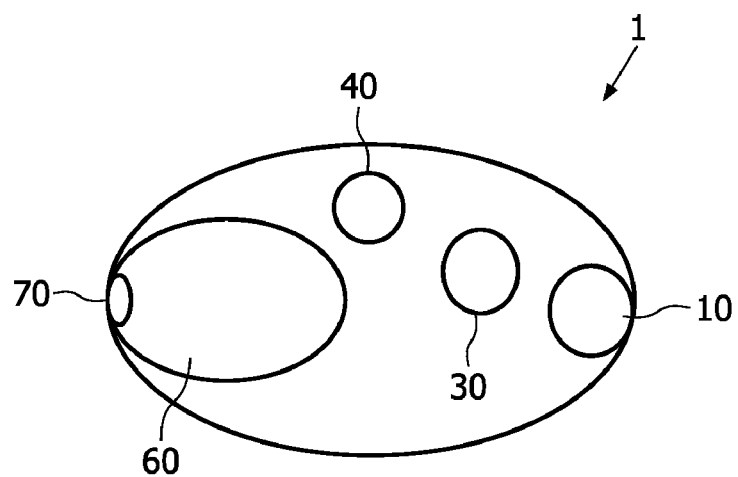
FIG. 1 is a highly schematic cross-sectional view of a device according to a first embodiment of the present invention.

The delivery of drugs itself is achieved in this example by a valve 70 which is controlled by the central control unit 30. Upon accordant signals from the central control unit 30, the valve 70 opens and allows drugs stored in a drug storage container 60 to flow from the device. According to another embodiment of the present invention (not shown in the FIGS.), the valve may be replaced by any other kind of dispensing system providing the delivery of a specified amount of drug.

It should be noted that, according to another embodiment, the measuring means 10 and the central control unit 30 may be outside the capsule 1; in which case the capsule 1 may contain a data sending and receiving means according to an embodiment of the present invention in order to receive a signal for the start of the drug release program.

The invention will be better understood from the following description of examples of some applications in which a device according to the present invention may be of use, which are definitely to be understood as examples not limiting the present invention.

EXAMPLE I

Application: Asthma

In an embodiment of the present invention, the measured body parameter is core body temperature. The drug release program is started when during the at least ≧1 monitoring cycle a decline of ≧40%/hour (on the normalized scale) has been observed in the normalized monitoring data for a period of ≧3 hours, whereupon the drug is delivered without delay.

According to an embodiment of the present invention, the drug release is stopped 9 hours after the start of the drug release program.

According to a different embodiment of the present invention, the drug release is stopped when during the at least ≧1 monitoring cycle a rise of ≧30%/hour (on the normalized scale) has been observed in the normalized monitoring data for a period of ≧4 hours.

Figure 2:
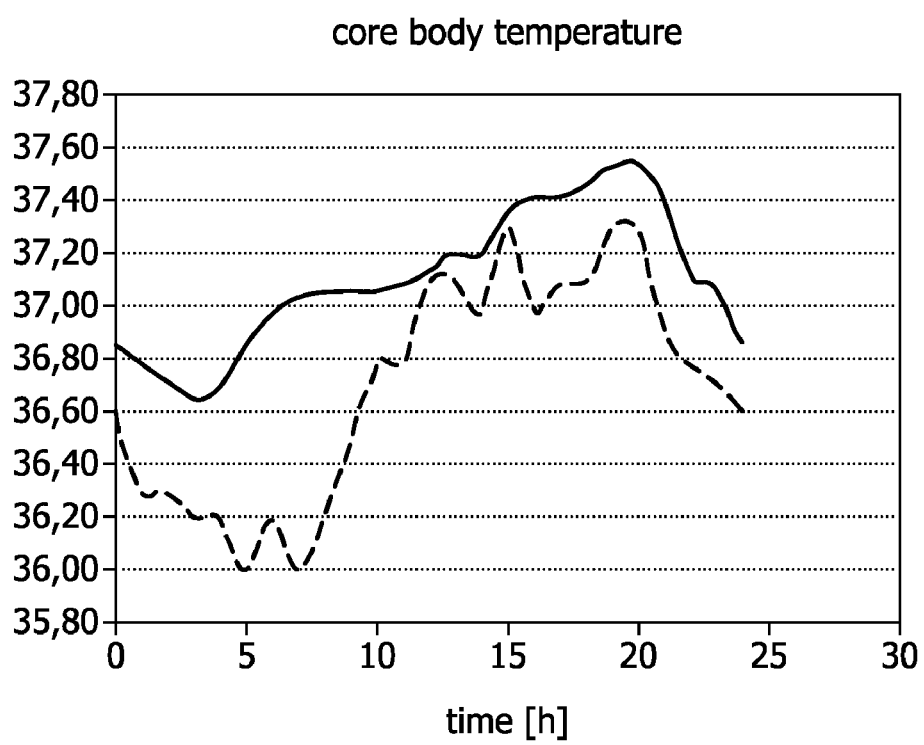
FIG. 2 is a diagram of core body temperature over time for two days for a certain patient (cf. Example I)
Figure 3:
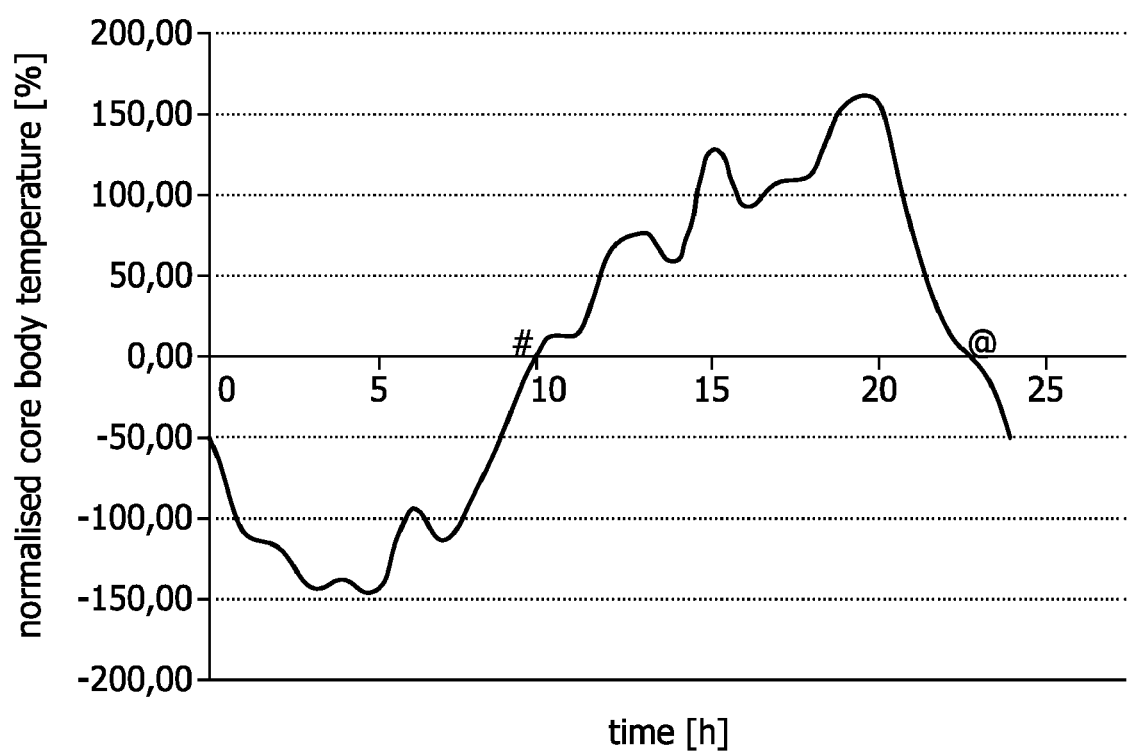
FIG. 3 shows a normalized curve derived from the data in FIG. 2.

This example is discussed in more detail, but purely by way of example, with reference to Table I and FIGS. 2 and 3.

Table I shows the core body temperature for a patient over two days, after which the average temperature and a normalized temperature were derived therefrom.

TABLE I

| time [h] | day 1 [° C.] | day 2 [° C.] | average temperature [° C.] | normalized temperature [%] |
|---|---|---|---|---|
| 0 | 36.60 | 36.87 | 36.74 | −49.72 |
| 1 | 36.30 | 36.78 | 36.54 | −108.33 |
| 2 | 36.30 | 36.72 | 36.51 | −117.35 |
| 3 | 36.20 | 36.65 | 36.43 | −142.90 |
| 4 | 36.20 | 36.68 | 36.44 | −138.39 |
| 5 | 36.00 | 36.84 | 36.42 | −144.40 |
| 6 | 36.20 | 36.97 | 36.59 | −94.80 |
| 7 | 36.00 | 37.04 | 36.52 | −114.34 |
| 8 | 36.20 | 37.06 | 36.63 | −81.28 |
| 9 | 36.50 | 37.07 | 36.79 | −34.69 |
| 10 | 36.80 | 37.07 | 36.94 | 10.40 |
| 11 | 36.80 | 37.10 | 36.95 | 14.91 |
| 12 | 37.10 | 37.13 | 37.12 | 64.50 |
| 13 | 37.10 | 37.21 | 37.16 | 76.53 |
| 14 | 37.00 | 37.20 | 37.10 | 60.00 |
| 15 | 37.30 | 37.36 | 37.33 | 129.13 |
| 16 | 37.00 | 37.42 | 37.21 | 93.06 |
| 17 | 37.10 | 37.42 | 37.26 | 108.09 |
| 18 | 37.10 | 37.46 | 37.28 | 114.10 |
| 19 | 37.30 | 37.53 | 37.42 | 154.68 |
| 20 | 37.30 | 37.55 | 37.43 | 157.68 |
| 21 | 36.90 | 37.42 | 37.16 | 78.03 |
| 22 | 36.80 | 37.13 | 36.97 | 19.42 |
| 23 | 36.70 | 37.07 | 36.89 | −4.63 |
| 24 | 36.60 | 36.87 | 36.74 | −49.72 |

FIG. 2 shows a diagram of the two temperature curves of Table I.

FIG. 3 shows a diagram of the normalized temperature of Table I.

On the time point indicated by a "@" in FIG. 3, the drug release program was started—according to the embodiment described above—and stopped (on the next day) on the time point indicated by a "#", i.e. after an increase as described above.

The drug in this example is theophylline.

EXAMPLE II

Application: Hypercholesterolemia

According to an embodiment of the present invention, the drug release program is started when during the at least $\geq 1$ monitoring cycle an increase of $\geq 25\%$/hour (on the normalized scale) has been observed in the normalized monitoring data for a period of $\geq 5$ hours. The body parameter is core body temperature, the drug program is started with a delay of 7 hours. The drug is HMG-CoA.

According to an embodiment of the present invention, the drug release is stopped when during the at least $\geq 1$ monitoring cycle the normalized monitoring data deviates from the normalized 0%-point of the normalized curve by a threshold value of $\leq 50\%$ accompanied by a decreasing temperature.

According to a different embodiment of the present invention, the drug release is stopped 8 hours after the start of the release of drugs, i.e. after 15 hours.

EXAMPLE III

Application: Paroxysmal Atrial Fibrillation

According to an embodiment of the present invention, the drug release program is started when during the at least $\geq 1$ monitoring cycle a decline of $\geq 40\%$/hour (on the normalized scale) has been observed in the normalized monitoring data for a period of $\geq 3$ hours. The body parameter is core body temperature, the drug program is started with a delay of 6 hours.

According to an embodiment of the present invention, the drug release is stopped when during the at least $\geq 1$ monitoring cycle the normalized monitoring data deviates from the normalized 0%-point of the normalized curve by a threshold value of $\leq 5\%$ accompanied by an increasing temperature.

EXAMPLE IV

Application: Acute Lymphoblastic Leukaemia (Pediatric)

According to an embodiment of the present invention, the drug release program is started when during the at least $\geq 1$ monitoring cycle an increase of $\geq 25\%$/hour (on the normalized scale) has been observed in the normalized monitoring data for a period of $\geq 5$ hours. The body parameter is core body temperature, the drug release program is started with a delay of 6 hours. The drug is selected from the group comprising 6-mercaptopurine, methotrexate, and mixtures thereof.

According to an embodiment of the present invention, the drug release is stopped when during the at least $\geq 1$ monitoring cycle the normalized monitoring data deviates from the maximum point of the normalized curve by a threshold value of $\leq 5\%$.

According to a different embodiment of the present invention, the drug release is stopped 5 hours after the start of the release of drugs, i.e. after 11 hours of the start of the drug release program.

EXAMPLE V

Application: Metastatic Colorectal Cancer

According to an embodiment of the present invention, the drug release means starts a drug release program when during the at least $\geq 1$ monitoring cycle the normalized monitoring data deviates from the maximum point of the normalized curve by a threshold value of $\leq 25\%$. The body parameter is core body temperature, the drug program is started with a delay of 1 hour. The drug is capecitabine.

According to an embodiment of the present invention, the drug release is stopped when during the at least $\geq 1$ monitoring cycle the normalized monitoring data deviates from the minimum point of the normalized curve by a threshold value of $\leq 25\%$.

According to a different embodiment of the present invention, the drug release is stopped 6 hours after the start of the release of drugs, i.e. after 7 hours of the start of the drug release program.

EXAMPLE VI

Application: Ovarian Cancer

According to an embodiment of the present invention, the drug release means starts a drug release program when during the at least $\geq 1$ monitoring cycle the normalized monitoring data deviates from the normalized 0%-point of the normalized curve by a threshold value of $\leq 25\%$ and is decreasing. The body parameter is core body temperature, the drug program is started with a delay of 4 hours. The drug is doxorubicin.

According to an embodiment of the present invention, the drug release is stopped when during the at least $\geq 1$ monitoring cycle the normalized monitoring data deviates from the minimum point of the normalized curve by a threshold value of $\leq 25\%$.

According to a different embodiment of the present invention, the drug release is stopped 12 hours after the start of the release of drugs, i.e. after 16 hours of the start of the drug release program.

EXAMPLE VII

Application: Breast Cancer Treatment

According to an embodiment of the present invention, the drug release means starts a drug release program when during the at least $\geq 1$ monitoring cycle the normalized monitoring data deviates from the maximum point of the normalized curve by a threshold value of $\leq 5\%$. The body parameter is core body temperature, the drug program is started without delay. The drug is cisplatin.

According to an embodiment of the present invention, the drug release is stopped when during the at least $\geq 1$ monitoring cycle the normalized monitoring data deviates from the minimum point of the normalized curve by a threshold value of $\leq 25\%$.

EXAMPLE VIII

Application: Rheumatoid Arthritis

According to an embodiment of the present invention, the drug release means starts a drug release program when during the at least $\geq 1$ monitoring cycle the normalized monitoring data deviates from the 0%-point of the normalized curve by a threshold value of $\leq 5\%$ at decreasing temperature. The body parameter is core body temperature, the drug program is started with a delay of 5 h. The drug is cyclooxygenase-2.

According to an embodiment of the present invention, the drug release is stopped when during the at least $\geq 1$ monitoring cycle the normalized monitoring data deviates from the normalized 0%-point of the normalized curve by a threshold value of $\leq 5\%$ and is increasing.

EXAMPLE IX

Application: Steoarthritis

According to an embodiment of the present invention, the drug release means starts a drug release program when during the at least ≧1 monitoring cycle the normalized monitoring data deviates from the normalized 0%-point of the normalized curve by a threshold value of ≦25% and is increasing. The body parameter is core body temperature, the drug program is started without delay. The drug is cyclooxygenase-2.

According to an embodiment of the present invention, the drug release is stopped when during the at least ≧1 monitoring cycle a decrease of ≧40%/hour (on the normalized scale) has been observed in the normalized monitoring data for a period of ≧3 hours.

According to a different embodiment of the present invention, the drug release is stopped 12 hours after the start of the drug release program.

The particular combinations of elements and features in the above embodiments are merely examples; the interchanging and substitution of these teachings with other teachings in this and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto. Furthermore, reference signs used in the description and claims do not limit the scope of the invention as claimed.

What is claimed is:

1. A medical device for drug administration comprising:
   a) a device which measures at least one body parameter of a patient for at least one measuring cycle and at least one monitoring cycle,
   b) a central control unit programmed to generate a normalized curve for each of the at least one measured body parameter of the patient from measured data obtained in the at least one measuring cycle and to adjust the measured data obtained in the at least one monitoring cycle to normalize the measured data based on the normalized curve to generate normalized monitoring data, and
   c) an ingestible capsule which starts releasing the drug in response to a change of at least 25%/hour on a normalized scale being observed in the normalized monitoring data for a period of at least 1 hour.

2. The device according to claim 1, wherein the at least one body parameter includes at least one of body temperature, core body temperature, skin surface temperature, blood pressure, melatonin level, triacylglycerol level, and cortisol level.

3. The device according to claim 1, wherein the central control unit controls the ingestible capsule to start releasing the drug during the at least one monitoring cycle in response to a change of at least 40%/hour on the normalized scale being observed in the normalized monitoring data for a period of at least 3 hours.

4. The device according to claim 1, wherein the central control unit controls the ingestible capsule to start releasing the drug during the at least one monitoring cycle in response to the normalized monitoring data deviating from a minimum point of the normalized curve by a threshold value of at most 25%.

5. The device according to claim 1, wherein the central control unit controls the ingestible capsule to start releasing the drug during the at least one monitoring cycle in response to the normalized monitoring data deviating from a maximum point of the normalized curve by a threshold value of at most 25%.

6. The device according to claim 1, wherein the central control unit controls the ingestible capsule to delay releasing of the drug for at most 2 measuring and/or monitoring cycles.

7. The device according to claim 1, wherein the central control unit controls the ingestible capsule to delay releasing of the drug for between 1 and 24 hours.

8. The device according to claim 1, wherein the central control unit controls the ingestible capsule to stop releasing the drug after one of:
   at most 30 cycles and
   when the normalized monitoring data return to between at least −60% and at most 60% of the preselected point of the normalized curve.

9. The device according to claim 1, wherein the drug is also released in response to the normalized monitoring data deviating from a preselected point on the normalized curve by more than a threshold value of at most 50% on a normalized scale.

10. A method for the controlled release of drugs from a capsule, comprising:
    a) measuring at least one body parameter of a patient for at least 3 measuring cycles and at least one monitoring cycle,
    b) generating a normalized curve for the measured body parameter of the patient;
    c) adjusting the measured body parameter obtained in the at least one monitoring cycle to normalize the measured body parameter based on the normalized curve to generate normalized monitoring data, and
    d) starting to release a drug during the at least one monitoring cycle in response to at least observing a change of at least 25% in the normalized measured body parameter for a period of one hour.

11. The method according to claim 10, wherein the measured body parameter includes at least one of body temperature, core body temperature, skin surface temperature, blood pressure, melatonin level, triacylglycerol level, and cortisol level.

12. The method according to claim 10, further comprising:
    starting the drug release program in response to observing a change of at least 40%/hour in the normalized measured body parameter for a period of at least 3 hours.

13. The method according to claim 10, further comprising:
    starting the drug release program in response to the normalized measured body parameter deviating from a minimum point of the normalized curve by a threshold value of at most 25%.

14. The method according to claim 10, further including:
    stopping release of the drug based on a rate of change in the normalized measured body parameter.

15. The method according to claim 10, further including:
    delaying starting to release the drug by at least 1 hour.

16. The method according to claim 10, further including:
    stopping release of the drug after at most 30 cycles or when the normalized measured body parameter returns to between −60% and 60% of the preselected point on the normalized curve.

17. The method according to claim 10, wherein the release of the drug is started in response to the normalized measured body parameter deviating from a preselected point of the normalized curve by a preselected percentage.

18. A drug administration device comprising:
an ingestible capsule;
a parameter monitor disposed in the ingestible capsule to measure at least one body parameter of a patient who has ingested the ingestible capsule;
a drug storage container disposed in the ingestible capsule which stores drugs;
a valve which is controllable to release the drugs in the drug storage container from the ingestible capsule; and
a control unit disposed in the ingestible capsule, the control unit receiving measured body parameter data from the parameter monitor, generating a normalized curve from the measured body parameter data over a plurality of monitoring cycles, normalizing the measured body parameter data, and controlling the valve to release the drugs in response at least to the normalized measured body parameter changing at a preselected rate for a preselected duration.

19. The device according to claim 18, wherein the control unit further controls the valve to release the drugs in response to the normalized body parameter deviating from a selected point on the normalized curve by a preselected threshold value.

* * * * *